US008602647B2

(12) United States Patent
Navarro

(10) Patent No.: US 8,602,647 B2
(45) Date of Patent: Dec. 10, 2013

(54) RADIATION BEAM ANALYZER AND METHOD

(76) Inventor: Daniel Navarro, Port St. Lucie, FL (US)

( * ) Notice: Subject to any disclaimer, the term of this patent is extended or adjusted under 35 U.S.C. 154(b) by 97 days.

(21) Appl. No.: 13/188,610

(22) Filed: Jul. 22, 2011

(65) Prior Publication Data

US 2011/0278444 A1    Nov. 17, 2011

Related U.S. Application Data

(63) Continuation-in-part of application No. 13/174,950, filed on Jul. 1, 2011, now abandoned, which is a continuation-in-part of application No. 13/018,869, filed on Feb. 1, 2011, now Pat. No. 8,093,549, which is a continuation of application No. 12/630,450, filed on Dec. 3, 2009, now Pat. No. 7,902,515.

(60) Provisional application No. 61/119,629, filed on Dec. 3, 2008, provisional application No. 61/141,751, filed on Dec. 31, 2008.

(51) Int. Cl.
*G01D 18/00* (2006.01)

(52) U.S. Cl.
USPC ............ 378/207; 378/18; 378/65; 250/252.1

(58) Field of Classification Search
USPC ............................ 378/18, 65, 207; 250/252.1
See application file for complete search history.

(56) References Cited

U.S. PATENT DOCUMENTS

| | | | |
|---|---|---|---|
| 4,401,406 A * | 8/1983 | Rovira | 414/589 |
| 4,538,071 A | 8/1985 | Bardoux et al. | |
| 4,988,866 A | 1/1991 | Westerlund | |
| 5,006,714 A | 4/1991 | Attix | |
| 5,511,107 A | 4/1996 | Sliski | |
| 5,621,214 A | 4/1997 | Sofield | |
| 5,627,367 A | 5/1997 | Sofield | |
| 5,635,709 A | 6/1997 | Sliski et al. | |
| 5,905,263 A | 5/1999 | Nishizawa et al. | |
| 6,207,952 B1 | 3/2001 | Kan et al. | |

(Continued)

FOREIGN PATENT DOCUMENTS

| | | |
|---|---|---|
| DE | 3145262 | 5/1983 |
| EP | 1447047 | 8/2004 |

(Continued)

OTHER PUBLICATIONS

Harling, Ok et al, Head Phantoms for Neutron Capture Therapy, Medical Physics, vol. 22, No. 5, May 1995, pp. 579-583, Woodbury, NY, US.

*Primary Examiner* — Allen C. Ho
(74) *Attorney, Agent, or Firm* — McHale & Slavin, P.A.

(57) ABSTRACT

A radiation beam analyzer for measuring the distribution and intensity of radiation produced by a radiation producing device. The analyzer employs a relative small tank of water into which a sensor is placed to maintain a constant SAD (source to axis distance). A first method maintains a fixed position of the sensor, and raises or lowers the small tank of water. A second method moves the sensor up, down or rotationally synchronously in opposite directions with respect to the small tank of water to keep the SAD constant. These methods position the sensor relative to the radiation source to simulate the location of a malady within a patient's body. The present invention enables measurements of substantially larger fields. This is accomplished by rotating a tank of water 90 degrees from a first position to a second position.

20 Claims, 18 Drawing Sheets

(56) References Cited

U.S. PATENT DOCUMENTS

| | | |
|---|---|---|
| 6,225,622 B1 | 5/2001 | Navarro |
| 6,720,766 B2 * | 4/2004 | Parker et al. ............. 324/308 |
| 7,056,019 B1 * | 6/2006 | Hanson et al. ............ 378/207 |
| 7,189,975 B2 | 3/2007 | Schmidt et al. |
| 7,193,220 B1 | 3/2007 | Navarro |
| 7,420,160 B2 | 9/2008 | Delaperriere et al. |
| 7,605,365 B2 * | 10/2009 | Chen et al. ............. 250/252.1 |
| 7,902,515 B2 | 3/2011 | Navarro |
| 8,093,549 B2 * | 1/2012 | Navarro ................. 250/252.1 |
| 8,183,522 B2 * | 5/2012 | Celi de la Torre et al. 250/252.1 |
| 8,321,179 B2 * | 11/2012 | Simon et al. ............. 702/189 |
| 2005/0173648 A1 | 8/2005 | Schmidt et al. |
| 2006/0033044 A1 | 2/2006 | Gentry et al. |
| 2008/0048125 A1 | 2/2008 | Navarro |

FOREIGN PATENT DOCUMENTS

| | | |
|---|---|---|
| WO | WO9714017 | 4/1997 |
| WO | WO200007037 | 2/2000 |
| WO | WO2008002689 | 1/2008 |
| WO | WO2008024614 | 2/2008 |
| WO | WO2010065740 A3 | 6/2010 |

* cited by examiner

RADIATION BEAM ANALYZER AND METHOD

CROSS REFERENCE TO RELATED APPLICATIONS

This application is a continuation-in-part of U.S. patent application Ser. No. 13/174,950, filed Jul. 1, 2011, now abandoned entitled "Radiation Beam Analyzer and Method", which is a continuation-in-part of U.S. patent application Ser. No. 13/018,869, filed Feb. 1, 2011, entitled "Radiation Beam Analyzer and Method," now U.S. Pat. No. 8,093,549, which is a continuation of U.S. patent application Ser. No. 12/630,450, filed Dec. 3, 2009, entitled "Radiation Beam Analyzer and Method," now U.S. Pat. No. 7,902,515, which application claims the benefit under 35 U.S.C. 119(e) of U.S. Provisional Patent Application Nos. 61/119,629, filed Dec. 3, 2008, entitled, "Cyberknife® Radiation Beam Analyzer and Method" and 61/141,751, filed Dec. 31, 2008, entitled, "Isocentric Radiation Beam Analyzer and Method". This application is also related to U.S. Patent Application No. 61/083,740, filed Jul. 25, 2008, entitled, "Modular Radiation Beam Analyzer Software"; U.S. patent application Ser. No. 11/510,275, filed Aug. 25, 2006, entitled, "Convertible Radiation Beam Analyzer System"; U.S. Pat. No. 7,193,220, issued Mar. 20, 2007, entitled, "Modular Radiation Beam Analyzer"; and U.S. Pat. No. 6,225,622, issued May 1, 2001, entitled "Dynamic Radiation Scanning Device." The entirety of these patent applications and patents are hereby incorporated by reference.

FIELD OF THE INVENTION

This invention relates to a method and device for measuring the radiation dose of a linear accelerator or other radiation producing device at a target, and particularly relates to the tracking and measurement of a radiation dose from a Cyberknife®, a linear accelerator or other radiation producing devices used in conjunction with a radiosurgery system for the non-invasive treatment of both cancerous and non-cancerous tumors anywhere in the human body including the prostrate, lung, brain, spine, liver, pancreas and kidney.

BACKGROUND OF THE INVENTION

Various well known medical techniques for the treatment of malignancies involve the use of radiation. Radiation sources, for example medical linear accelerators, are typically used to generate radiation which is directed to a specific target area of a patient. Proper doses of radiation directed at the malignant area of the patient are of the upmost importance. When properly applied, the radiation produces an ionizing effect on the malignant tissues of the patient, thereby destroying the malignant cells. As long as the dosimetry of the applied radiation is properly monitored, the malignancy can be treated without any detriment to the surrounding healthy body tissue. The goal of these treatments is to focus a high dose of radiation to a tumor or malignant cells while minimizing the exposure of the surrounding healthy tissue to the radiation. Accelerators may be utilized to deliver the radiation. Different accelerators have varying characteristics and output levels. The most common type of accelerator produces pulse radiation. The output beam has a rectangular shape in cross section and a cross sectional area typically between 1 and 1,600 square centimeters ($cm^2$). Preferably, the cross sectional area or field size is between 1×1 square centimeters ($cm^2$) and 40×40 square centimeters ($cm^2$). Rectangular or square cross sectional shapes are often changed to any desired cross sectional shape using molded or cast lead or cerrobend materials. More advanced accelerators use multi-leaf collimators. Other accelerators are continuously or non-pulsed, such as cobalt radiation machines. Some accelerators utilize a swept electron beam, which passes a very narrow electron beam across the treatment field by means of varying electromagnetic fields.

To ensure proper dosimetry, linear accelerators used for the treatment of malignancies must be calibrated. Both the electron and photon radiation must be appropriately measured and correlated to the particular device. The skilled practitioner must insure that both the intensity and duration of the radiation treatment is carefully calculated and administered so as to produce the therapeutic result desired while maintaining the safety of the patient. Parameters such as flatness, symmetry, radiation and light field alignment are typically determined. The use of too much radiation may, in fact, cause side effects and allow destructive effects to occur to the surrounding tissue. Use of an insufficient amount of radiation will not deliver a dose that is effective to eradicate the malignancy. Thus, it is important to be able to determine the exact amount of radiation that will be produced by a particular machine and the manner in which that radiation will be distributed within the patient's body.

In order to produce an accurate assessment of the radiation received by the patient, at the target area, some type of pattern or map of the radiation at varying positions within the patient's body must be produced. These profiles correlate: 1) the variation of dose with depth in water generating percent depth dose profiles, 2) the variation of dose across a plane perpendicular to the radiation source generating the cross beam profiles, and 3) the variation of dose with depth in water generating percent depth dose and TMR/TPR (Tissue Maximum Ratio/Tissue Phantom Ratio) when the SAD (source to axis distance) is constant profiles. These particular measurements of cross beam profiles are of particular concern in the present invention. Although useful for other analyses, the alignment of the cross profiles in both radial and transverse planes are the basis of the present invention.

There are companies that provide the calibration service to hospitals and treatment centers. These physicists must visit the facility and conduct the calibration of the radiation source with their own equipment. This requires lightweight, easily portable, less cumbersome radiation measuring devices that can be quickly assembled and disassembled on site. The actual scanning should also be expeditious with the results available within a short time frame. Such equipment allows a physicist to be more efficient and calibrate more radiation devices in a shorter period of time.

One existing system for measuring the radiation that is produced by medical linear accelerators utilizes a large tank on the order of 50 cm×50 cm×50 cm filled with water. A group of computer controlled motors move the radiation detector through a series of pre-programmed steps along a single axis beneath the water's surface. Since the density of the human body closely approximates that of water, the water-filled tank provides an appropriate medium for creating a simulation of both the distribution and the intensity of radiation which would likely occur within the patient's body. The aforementioned tank is commonly referred to as a water phantom. The radiation produced by the linear accelerator will be directed into the water in the phantom tank, at which point the intensity of the radiation at varying depths and positions within the water can be measured with the radiation detector. As the radiation penetrates the water, the direct or primary beam is scattered by the water, in much the same way as a radiation beam impinging upon the human patient. Both the scattered radiation, as well as the primary radiation, are detected by the ion-chamber, which is part of the radiation detector or by radiation sensitive diodes.

The ion-chamber is essentially an open air capacitor which produces an electrical current that corresponds to the number of ions produced within its volume. The detector is lowered to a measurement point within the phantom tank and measurements are taken over a particular time period. The detector can then be moved to another measurement point where measurements are taken as the detector is held in the second position. At each measuring point a statistically significant number of samples are taken while the detector is held stationary.

In radiation therapy and radiosurgery, for example, a tumor may be non-invasively destroyed by a beam of ionizing radiation that kills the cells in the tumor. It is desirable to direct the radiation beam only to the tumor and not to the healthy tissue which surrounds the tumor. Therefore, accurate aiming of the beam at the tumor is extremely important in these radiation treatments. The goal is to focus a high dose of radiation to the tumor while minimizing the exposure of the surrounding healthy tissue to radiation. For adequate distribution of radiation dosage to the tumor, the direction of the radiation beam is typically adjusted during the treatment to track the tumor.

The most advanced modern radiosurgery systems, such as the Cyberknife® Robotic Radiosurgery System of Accuray, Inc., utilizes stereo online x-ray imaging during treatment to enhance the accuracy of the radiation treatment. The position of a patient's bony landmarks, e.g. their skull, can be determined with high accuracy by using the Cyberknife® stereo x-ray camera system. Thus, this highly accurate x-ray camera system can be used to treat a target region if the position of the target region relative to a bony landmark remains constant. However, the x-ray camera system cannot be used to determine the position of a target region if the position of the target region relative to a bony landmark changes because the target, e.g. a tumor, is generally not visible in x-ray images. For example, a target region in a patient's abdomen or chest cannot be treated with this method alone.

An image guidance system is essential to the proper operation of the Cyberknife® system. The first method developed for controlling the image guidance system was known as 6D or skull based tracking. An X-ray camera produces images which are compared to a library of computer generated images of the patient anatomy Digitally Reconstructed Radiographs (DRR's), and a computer algorithm determines what motion corrections have to be given to the robot because of patient movement. This imaging system allows the Cyberknife® to deliver radiation with an accuracy of 0.5 mm without using mechanical clamps attached to the patient's skull. The use of the image guided technique is referred to as frameless stereotactic radiosurgery. This method is referred to as 6D because corrections are made for the 3 translational motions (X, Y and Z) and three rotational motions.

DESCRIPTION OF THE PRIOR ART

Several prior art devices are known to teach systems for ascertaining the suitable dosimetry of a particular accelerator along with methods for their use.

U.S. Pat. Nos. 5,621,214 and 5,627,367, issued to Sofield, are directed to a radiation beam scanner system which employs a peak detection methodology. The device includes a single axis mounted within a water phantom. In use, the water phantom must be leveled and a reference detector remains stationary at some point within the beam while the signal detector is moved up and down along the single axis by the use of electrical stepper motors. While these devices employ a water phantom, they are limited to moving the signal detector along the single axis and can only provide a planar scan of the beam.

U.S. Patent Application Publication 2006/0033044 A1, now U.S. Pat. No. 7,202,486, to Gentry et al., is directed to a treatment planning tool for multi-energy electron beam radiotherapy. The system consists of a stand-alone calculator that enables multi-energy electron beam treatments with standard single electron beam radio-therapy equipment thereby providing improved dose profiles. By employing user defined depth-dose profiles, the calculator may work with a wide variety of existing standard electron beam radiotherapy systems.

U.S. Pat. No. 6,225,622, issued May 1, 2001, to Navarro, the inventor herein, describes a dynamic radiation measuring device that moves the ion chamber through a stationary radiation beam to gather readings of radiation intensity at various points within the area of the beam. The disclosure of this patent is incorporated herein, by reference.

U.S. Pat. No. 4,988,866, issued Jan. 29, 1991, to Westerlund, is directed toward a measuring device for checking radiation fields from treatment machines used for radiotherapy. This device comprises a measuring block that contains radiation detectors arranged beneath a cover plate, and is provided with field marking lines and an energy filter. The detectors are connected to a read-out unit for signal processing and presentation of measurement values. The dose monitoring calibration detectors are fixed in a particular geometric pattern to determine homogeneity of the radiation field. In use, the measuring device is able to simultaneously check the totality of radiation emitted by a single source of radiation at stationary positions within the measuring block.

U.S. Pat. No. 7,189,975, issued to Schmidt et al., is directed to a wire free, dual mode calibration instrument for high energy therapeutic radiation. The apparatus includes a housing with opposed first and second faces holding a set of detectors between the first and second faces. A first calibrating material for electrons is positioned to intercept electrons passing through the first face to the detectors, and a second calibrating material for photons is positioned to intercept photons passing through the second face to those detectors.

These devices do not use a water phantom and are additionally limited in that all of the ionization detectors are in one plane. This does not yield an appropriate three-dimensional assessment of the combination of scattering and direct radiation which would normally impinge the human body undergoing radiation treatment. Thus, accurate dosimetry in a real-life scenario could not be readily ascertained by the use of these devices.

U.S. Pat. No. 5,006,714, issued Apr. 9, 1991, to Attix, utilizes a particular type of scintillator dosimetry probe which does not measure radiation directly, but instead measures the proportional light output of a radiation source. The probe is set into a polymer material that approximates water or muscle tissue in atomic number and electron density. Attix indicates that the use of such a detector minimizes perturbations in a phantom water tank.

Additionally, there is an apparatus called a Wellhofer bottle-ship which utilizes a smaller volume of water than the conventional water phantom. The Wellhofer device utilizes a timing belt and motor combination to move the detector through the water, thus requiring a long initial set-up time.

Thus, there exists a need for a portable, modular radiation beam measuring device. The device should be capable of rapid assembly and disassembly for use at various locations to calibrate various Cyberknife® systems. The device should be capable of repeatable, accurate detection of the radiation emitted from the Cyberknife®. Since the distance between the Cyberknife® and the item being treated, e.g. a tumor, remains constant with this system, the device should also utilize a relative small volume of water or other fluid.

None of the above prior art devices are capable of performing fast and accurate isocentric measurements that result in direct measurement of the TMR/TPR (Tissue Maximum Ratio/Tissue Phantom Ratio) in depth and isocentric cross profiles. There also exists a need for a portable, modular radiation beam measuring device. The device should be capable of rapid assembly and disassembly for use at various locations to calibrate various isocentric radiation beam systems. The device should be capable of repeatable, accurate detection of the radiation emitted from the radiation source. Since the distance between the isocentric radiation beam source and the item being treated, e.g. a tumor, remains constant with this system, the device should also be capable of utilizing a relative small volume of water. Additionally, in the radiation treatment planning currently employed, the input sent to the radiation treatment planning computerized system is from non-isocentric data (SSD) which is then converted to isocentric data (SAD). This presents two major problems. First, the conversion algorithms used for the conversion are complicated. Second, the results are inaccurate. Thus, there is a need for a quick and accurate device to perform isocentric measurements for radiation treatment planning.

SUMMARY OF THE INVENTION

A first embodiment of the invention embodies a radiation beam analyzer for measuring the distribution and intensity of radiation produced by the Cyberknife® or other radiation producing machine. The analyzer employs a relatively small tank of water into which a sensor is placed. The distance between the sensor and the radiation source is not varied. The tank of water is raised and lowered relative to the sensor to simulate the location of a malady within a patient's body. This movement of the tank permits the radiation from the Cyberknife®, or other radiation producing machine, to be properly calibrated and adjusted for a proper treatment of a malady in a patient.

Another embodiment of the invention embodies a radiation beam analyzer for measuring the distribution and intensity of radiation produced by a radiation source. The analyzer employs a relatively small tank of water into which a sensor or detector is placed. The distance between the sensor and the radiation source is not varied. There are two methods to maintain the SAD (source to axis distance) constant. A first method maintains the position of detector fixed, utilizing a holder designed to retain the detector, and raises or lowers the small tank of water. A second method moves the detector up or down with a raising and lowering mechanism in one direction and synchronically moves the small tank of water in the opposite direction with another raising and lowering mechanism. The second method also keeps the SAD constant. These methods position the detector relative to the radiation source to simulate the location of a malady within a patient's body. This movement of the tank permits the radiation from the isocentric radiation beam source to be properly isocentrically measured.

A third embodiment of the present invention enables measurements of substantially larger fields than the first two embodiments. This is accomplished by rotating the tank up to 90 degrees from a first position to a second position.

Accordingly, it is an objective of the present invention to provide an accurate measurement of the radiation from a linear accelerator or the Cyberknife® used to perform radiosurgery or to treat a malady.

It is a further objective of the present invention to accurately position a linear accelerator or the Cyberknife® relatively to a malady in a patient's body.

It is yet another objective of the present invention to provide a modular radiation device including a relatively small tank of water which is moved relative to a fixed sensor in order to determine the proper amount of radiation required to treat a malady.

It is a still further objective of the present invention to provide a system and method for electronically controlling the movement of a tank of water and the measurement of radiation from a Cyberknife®.

It is a still further objective of the present invention to provide a mechanism to rotate a tank of water to enable accurate positioning of a linear accelerator.

It is a still further objective of the present invention to provide a mechanism to rotate a treatment table on which a patient is resting to enable accurate positioning of a linear accelerator.

It is a further objective of the present invention to accurately position the radiation detector, as well as obtain high repeatability of the measurements.

It is yet another objective of the present invention to provide a modular radiation device including a relatively small tank of water which is moved relative to a fixed detector or sensor in order to determine the proper amount of radiation required to treat a malady.

It is a still further objective of the present invention to provide a system and method for electronically controlling the movement of a relatively small tank of water and the movement of a detector or sensor mounted within the tank for the measurement of radiation from an isocentric radiation beam source.

It is still yet another objective of the present invention to provide a system wherein relative beam radiation data from 0.4 cm to 40 cm can be scanned and analyzed.

It is still a further objective of the present invention to provide a system having a modular design which can be applied to a 1-D (imensional), 2-D and 3-D systems.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
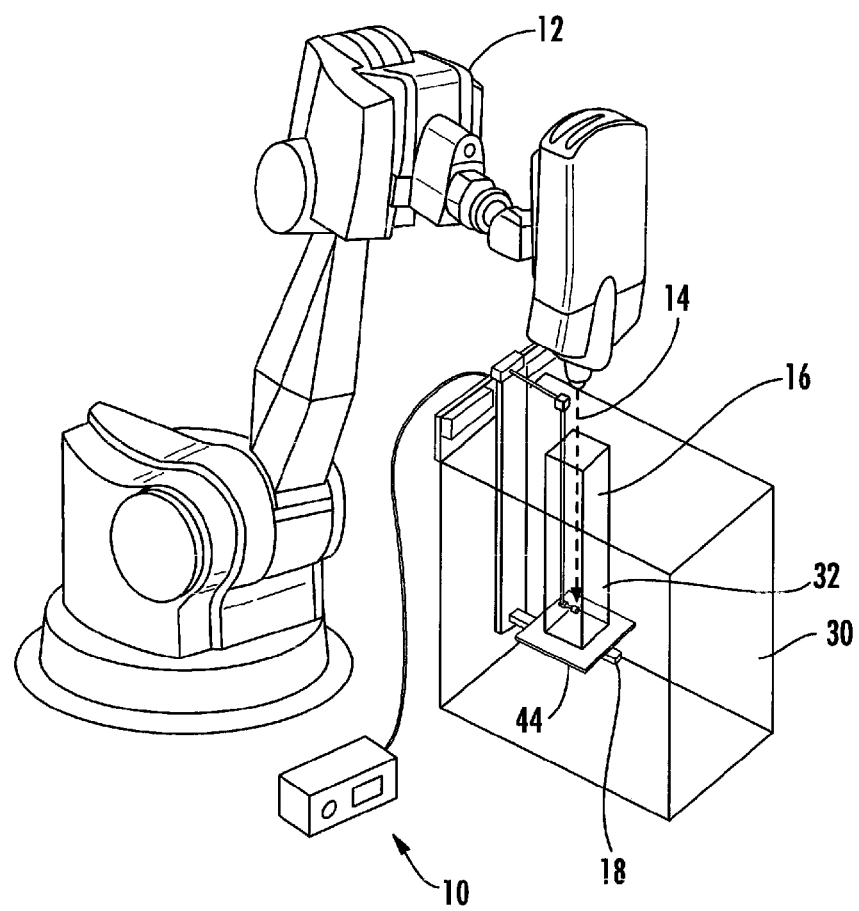
FIG. 1 is a perspective view of one embodiment of the present invention in use measuring the radiation from a Cyberknife®.
Figure 2:
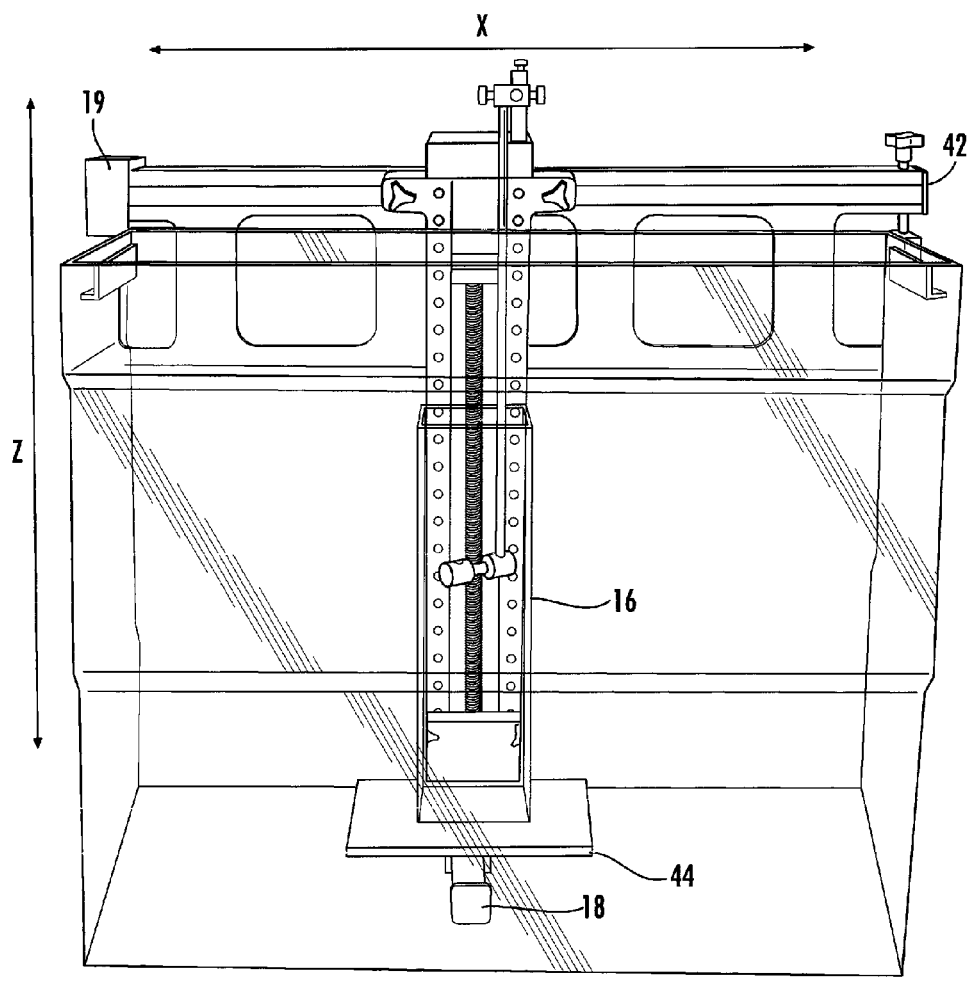
FIG. 2 is a front view of one embodiment of the present invention.
Figure 3:
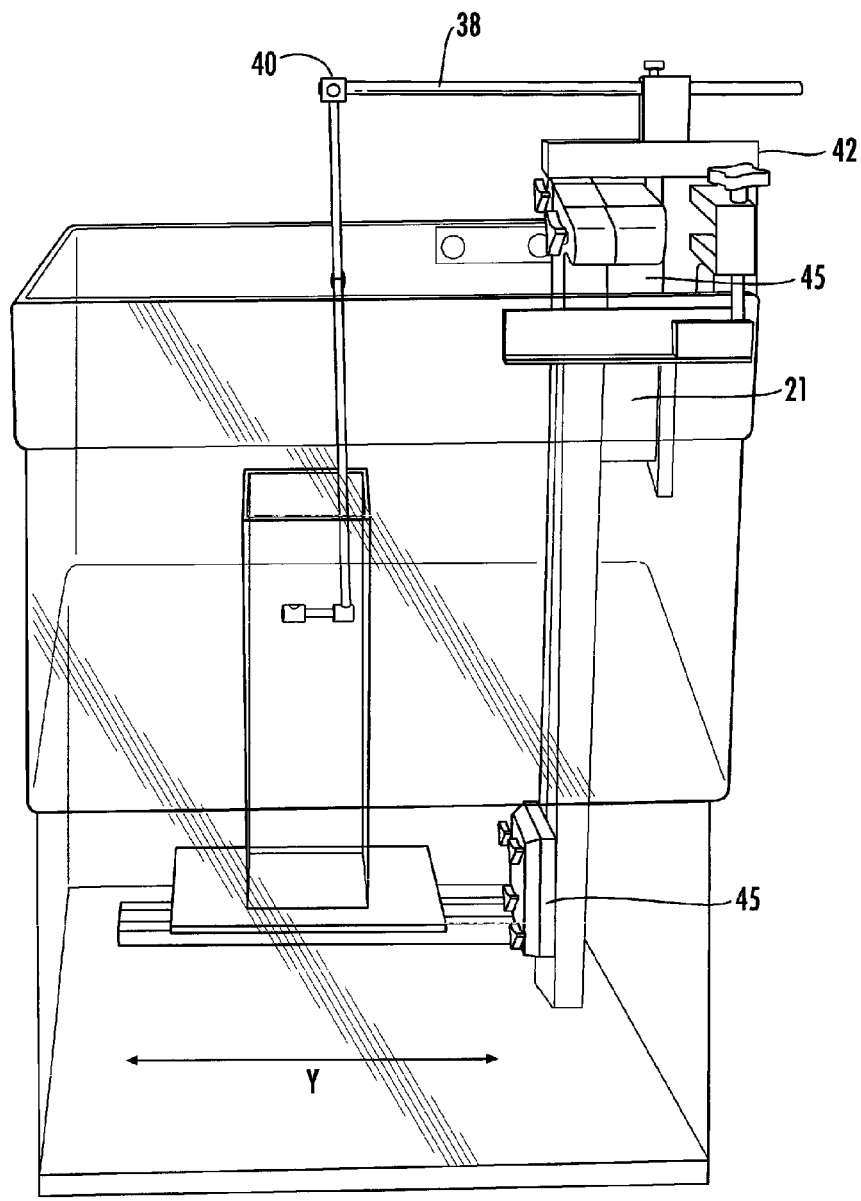
FIG. 3 is a side view of one embodiment of the present invention.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

The present invention is designed to measure with accuracy, precision and speed the radiation beams produced by a Cyberknife® or other radiation producing device. The Dynamic Phantom and Direct TMP/TPR Direct Measurement of radiation from a device utilized in radiosurgery have been previously described in applicant's related patent applications referred to herein. A combination of these two measurement methods and modifications of some of the features of these measurement methods has resulted in the present invention which will be described hereinafter.

Although the two basic concepts of Dynamic Phantom and Direct TMR/TPR Direct measurements are the same, the present invention requires water, not solid water like the Dynamic Phantom and is different from TMR/TPR. The radiation is imparted with the radiation source on the top of a tank, not laterally like in applicant's previous TMR/TPR measurements. The present invention also permits the use of a tank with a significantly smaller capacity. In a preferred embodiment of the present invention, the tank's capacity is 2.5 liters versus a prior art tank's capacity of 100 liters.

Referring to FIGS. 1-6, a first embodiment of the invention including a modular radiation beam analyzer 10 for measuring the distribution and intensity of radiation produced by a Cyberknife® 12 in a radiosurgery system is illustrated. A radiation beam 14 is emitted by a Cyberknife® in a substantially vertical direction. The beam 14 is very sharp and can be positioned on a patient with accuracy of less than one millimeter. The beam 14 is used to treat areas on a patient which preferably have a minimum field size of 0.5 cm in diameter and a maximum field size of 6 cm in diameter. The radiosurgery system, in which the Cyberknife® is employed, requires that all the radiation measurements be taken utilizing the isocentric method or direct measurement of TMR/TPR (Tissue Maximum Ratio/Tissue Phantom Ratio). In addition, because of the accuracy of this radiosurgery procedure, the measurements of the radiation require extreme accuracy.

The relatively small tank of the present invention is placed onto a carriage 18 of a measurement device which employs a substantially larger tank 30. The larger measurement device allows the carriage 18 to be moved in three different axes, X, Y and Z. The X axis extends along a horizontal portion of the tank 30 and can be seen in FIG. 2. The Z axis extends in the vertical direction and can also be seen in FIG. 2. The Y axis extends toward and away from a rear wall of the tank 30 and can be seen in FIG. 3. Small motors, such as a stepper motor, move the carriage 18 along all three axes. The present invention includes a second tank 16 that is movable in the Z direction only. While a stepper motor is a preferred embodiment, any type of motor or device which can move the carriage 18 along each of the three axes can be utilized.

In radiosurgery systems which utilize the Cyberknife®, the distance between the Cyberknife® and the malady being treated on a patient, such as a tumor, remains constant. Thus, in order to simulate the different positions or depths in a patient's body that the tumor or other malady being treated may be located, only the relative depth of the water, which simulates the depth of the item within a patient's body, needs to be varied. Once the correct depth or position within a patient's body is simulated by moving a sensor 32 to a specific depth in the water within the second tank 16 the amount of radiation from the Cyberknife® can be regulated to properly treat the tumor or malady. The present invention accomplishes this by moving the second tank 16 vertically up and down along the Z axis. This is illustrated in FIGS. 1-6.

Figure 4:
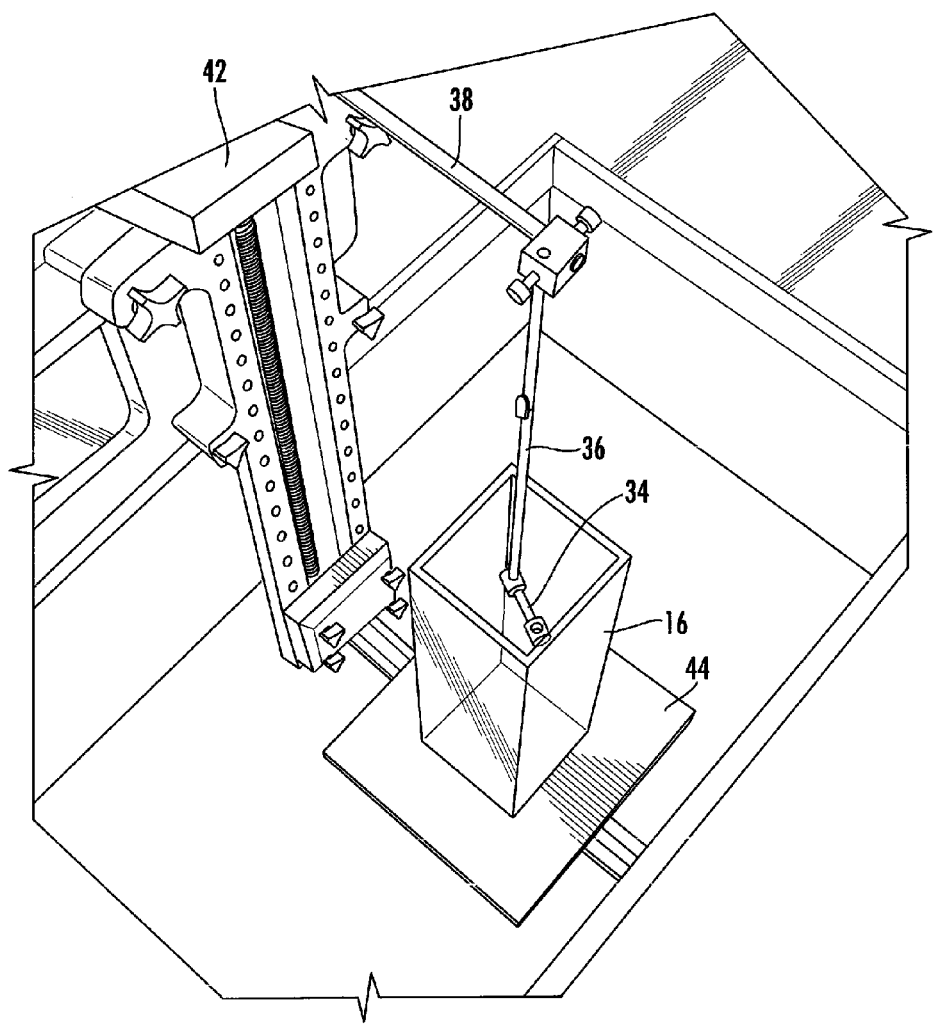
FIG. 4 is a top perspective view of one embodiment of the present invention.
Figure 5:
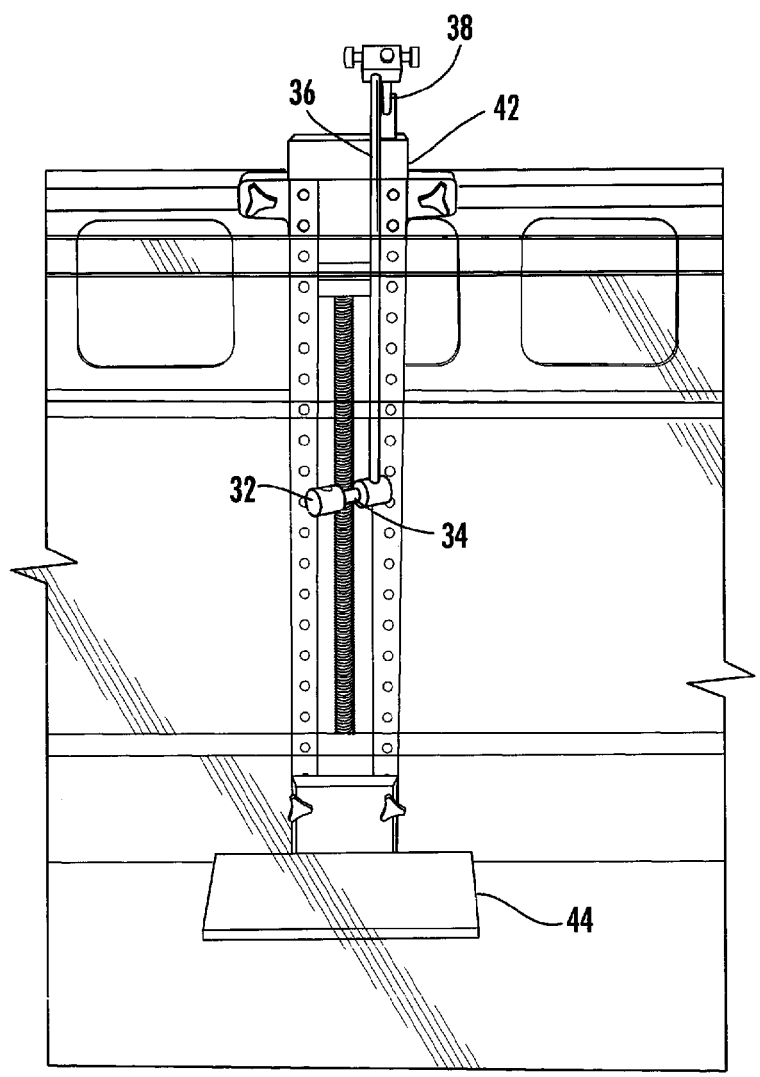
FIG. 5 is an enlarged front view of one embodiment of the present invention.
Figure 6:
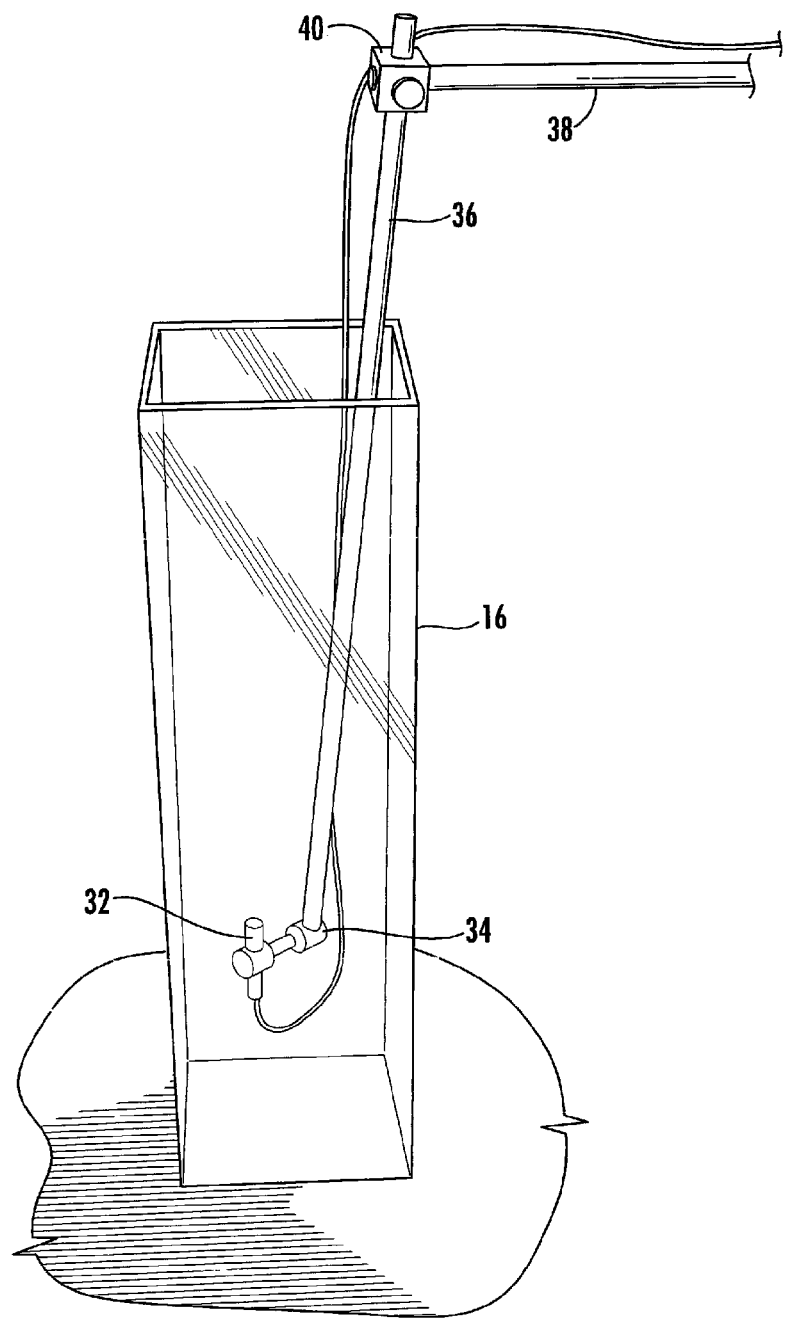
FIG. 6 is an enlarged front perspective view of one embodiment of the measurement tank of the present invention.

The sensor 32 is mounted on or positioned within a support 34, FIGS. 4, 5 and 6. The support 34 is secured onto a substantially vertical rod or support 36. The support 36 is in turn connected to and supported on a substantially horizontal rod or support 38. While a preferred connection device 40 is illustrated which applies a transverse force on supports 36 and 38, any other type of connection device 40 could also be employed. Support or rod 38 is connected to a guideway 42, FIG. 3, utilizing a connection device 40 mounted on the guideway. The support 34 permits the distance between the Cyberknife® 12 and the sensor 32 to be adjusted to simulate the distance between a commercial Cyberknife® and the malady being treated. The supports 38 and 34 permit the sensor 32 to be aligned with the radiation beam 14 from the CyberKnife® 12.

A stepper motor or other similar device 19 (FIG. 8) moves the carriage 18 along the X axis. A stepper motor or other similar device 21 (FIG. 4) moves the carriage 18 along the Z axis. This simulates the depth or level into which a malady is located within a patient's body. A stepper motor or other similar device 45 (FIG. 3) moves the carriage 18 along the Y axis. The carriage 18 has a support plate or platform 44 secured thereon, FIG. 5. The lower portion of second tank 16 is removably secured to the platform 44 so that the tank will not fall off the carriage 18 during operation of the present invention. There are various methods of securing second tank 16 to platform 44 including but not limited to fastening, gluing, welding, etc. While in the preferred embodiment, the second tank 16 is releasably secured to platform 44; it could also be permanently attached thereto.

While the second tank 16 is illustrated as substantially square in cross section and rectangular in height, a preferred embodiment is cylindrical. The cylinder is preferably 19 cm in diameter and 40 cm high. It is made from a clear acrylic material. Tanks having various other dimensions and weights can also be utilized. Tanks can also be made from various other materials.

This embodiment of the present invention utilizes the software and programming of applicant's U.S. patent application Ser. No. 61/083,740, filed Jul. 25, 2008, entitled, "Modular Radiation Beam Analyzer Software" and U.S. patent application Ser. No. 11/510,275, filed Aug. 25, 2006, entitled, "Convertible Radiation Beam Analyzer System" to control the motors which operate the guideways, to acquire data, to analyze the data, to provide graphical representations of the data and to transfer data with the pertinent modifications.

This embodiment of the present invention can be used with a single or an array of ion chambers. It can also be used with a plurality of diodes. The present invention can also be utilized with conventional radiation therapy. When used with conventional radiation therapy the dimensions of the second tank 16 are 14 cm long by 14 cm wide by 40 cm high.

Another embodiment of the present invention is designed to isocentrically measure with accuracy, precision and speed the radiation beams produced by a radiation beam source. This second embodiment of the present invention can also be used with a Cyberknife® radiation system. The dynamic phantom measurement of radiation and direct measurement of TMR/TPR (Tissue Maximum Ratio/Tissue Phantom Ratio) functions from a device utilized in radiosurgery have been previously described in applicant's related patent applications referred to herein. A combination of these two measurement methods and modifications of some of the features of these measurement methods has resulted in the present invention which will be described hereinafter. An isocentric radiation treatment system maintains the distance between the radiation source and the malady of a patient constant. In other words the SAD (source to axis distance) is constant. The radiation source can also be pivoted around the patient utilizing a manipulator 116 as illustrated in FIGS. 7 and 15.

There are two methods to maintain the SAD (source to axis distance) constant. A first method maintains the sensor in a fixed position; utilizing a holder designed to retain the sensor, and raises or lowers the small tank of water, as illustrated in FIGS. 1-6, 8, and 9. A second method moves the sensor up or down with a raising and lowering mechanism in one direction and synchronically moves the small second tank of water in the opposite direction with another raising and lowering mechanism, as illustrated in FIGS. 10-14. The second method also keeps the SAD constant. These methods position the sensor relative to the radiation source to simulate the location of a malady within a patient's body. This movement of the tank permits the radiation from the radiation beam source to be properly isocentrically measured.

Although the two basic concepts of dynamic phantom measurement and direct measurement of TMR/TPR functions are the same, this embodiment of the present invention can use water instead of solid water like the dynamic phantom measurement to measure cross beam profiles. This second embodiment of the present invention can also perform direct measurements of TMR/TPR with the radiation being imparted from source on the top of a tank, not laterally like in applicant's previous TMR/TPR measurements. Finally, combining these two concepts it is possible with a single device to isocentrically measure relative depth dose (TMR/TPR) and cross beam profiles. With the previous inventions two different devices were required. This second embodiment of the present invention also permits the use of a tank of water with a significantly smaller capacity than employed in prior art measurement systems. In a preferred embodiment the tank's capacity is 2.5 liters versus a prior art tank's capacity of 100 liters.

Figure 7:
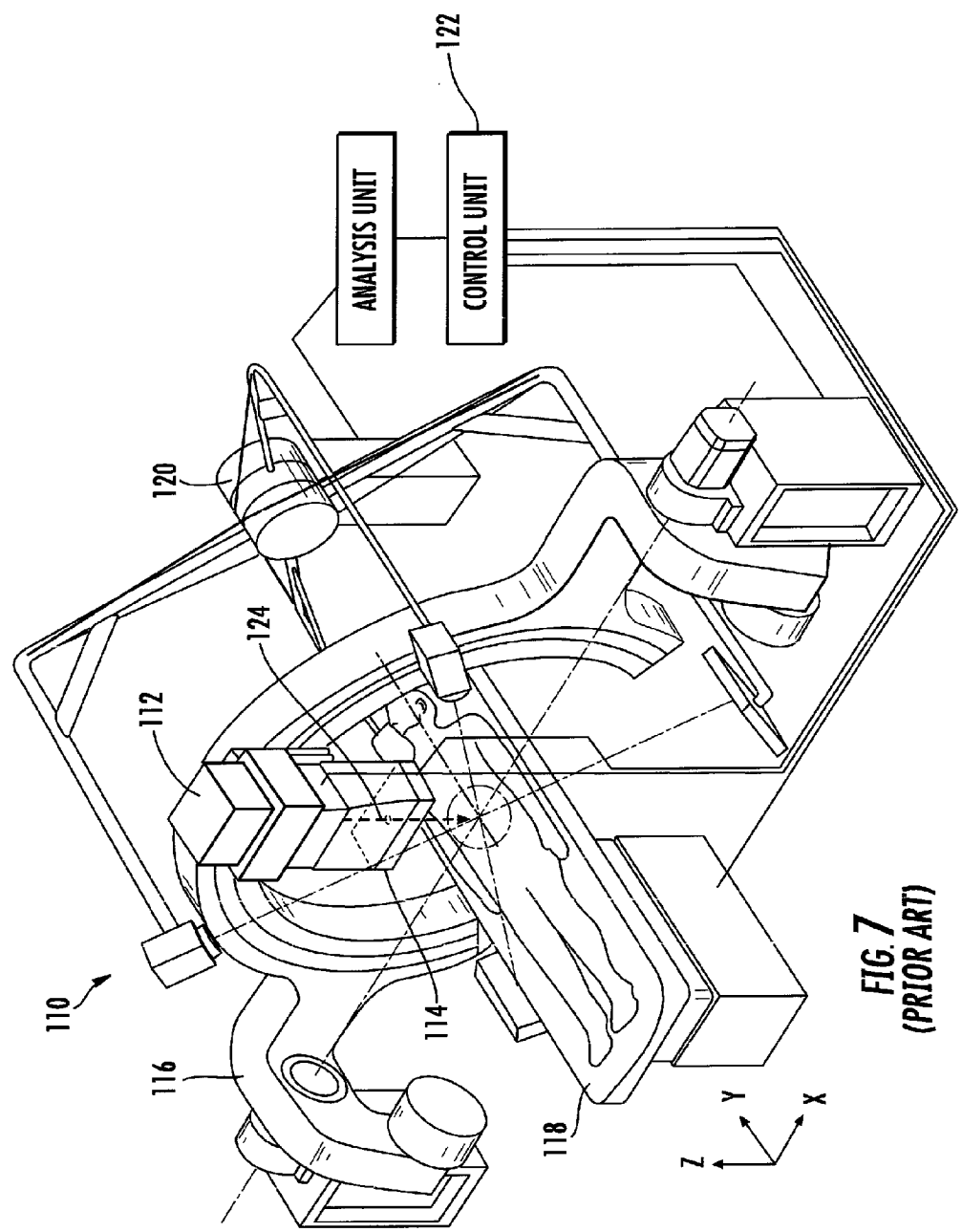
FIG. 7 is a perspective view of the prior art radiation treatment system utilizing an isocentric radiation beam source to treat a patient.
Figure 15:
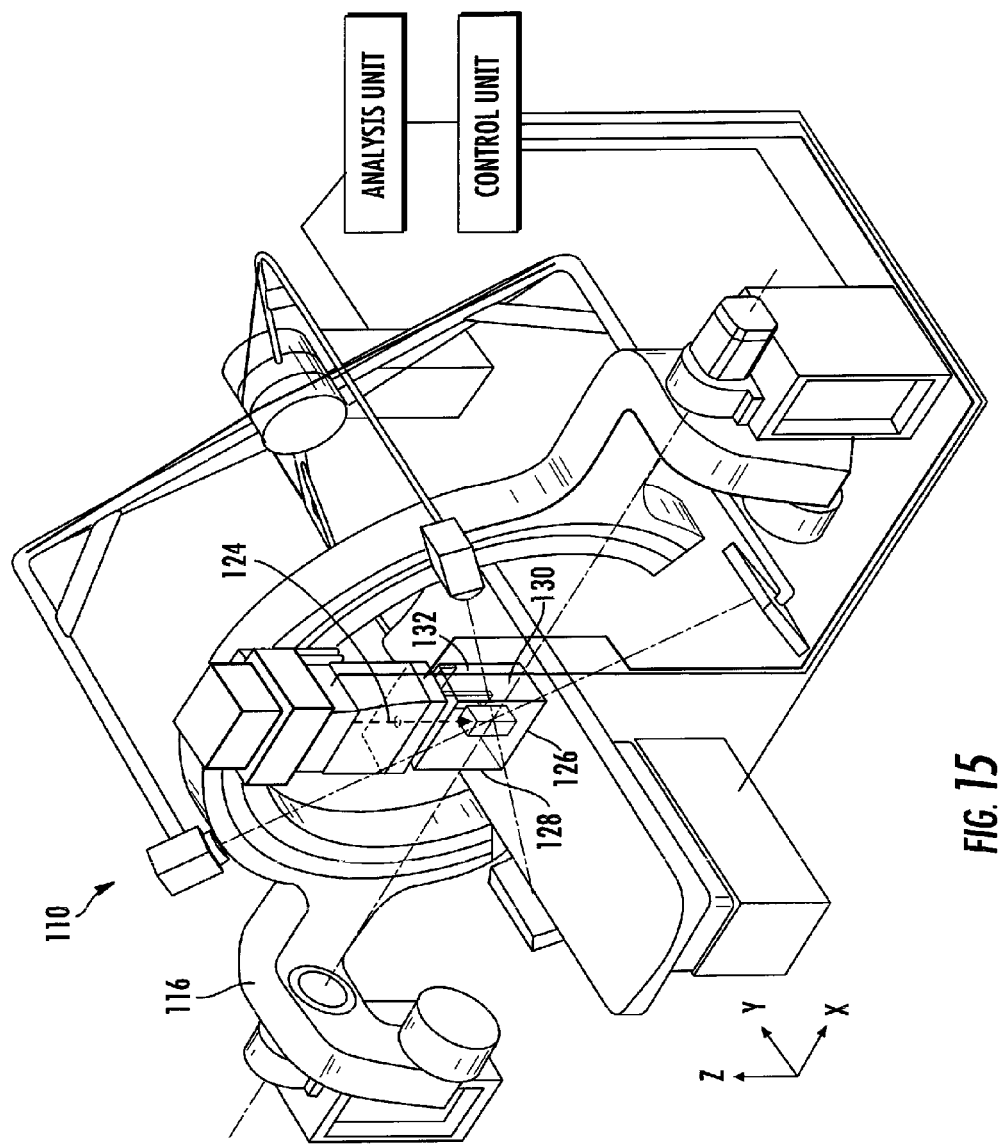
FIG. 15 is a perspective view of one embodiment of the present invention in use measuring the radiation from an isocentric radiation beam source.

Referring now to FIGS. 7 and 15, a prior art isocentric radiation treatment apparatus 110 is illustrated in FIG. 7. The isocentric radiation treatment apparatus illustrated in FIG. 7 comprises a radiation generation unit 112, a variable collimator 114, a manipulator 116, a movable treatment table 118, a diagnosis imager 120, and a control unit 122 which produces a radiation beam 124. The modular radiation beam analyzer 126 of the present invention for measuring the distribution and intensity of radiation produced by an isocentric radiation beam 124 in a radiosurgery system is illustrated in FIG. 15. The radiation beam 124 is emitted by an isocentric radiation beam source in a substantially vertical direction. The radiation beam 124 is very sharp and can be positioned on a patient with accuracy of less that one millimeter. The beam 124 is used to treat areas on a patient which preferably have a minimum field size of 0.5 cm in diameter and a maximum field size of 6 cm in diameter. The radiosurgery system, in which the isocentric radiation beam is employed, requires that all the radiation measurements be taken utilizing the isocentric method of direct measurement of TMR/TPR (Tissue Maximum Ratio/Tissue Phantom Ratio) of the present invention. In addition, because of the accuracy of this radiosurgery procedure, the measurements of the radiation delivered to the patient require extreme accuracy.

Figure 8:
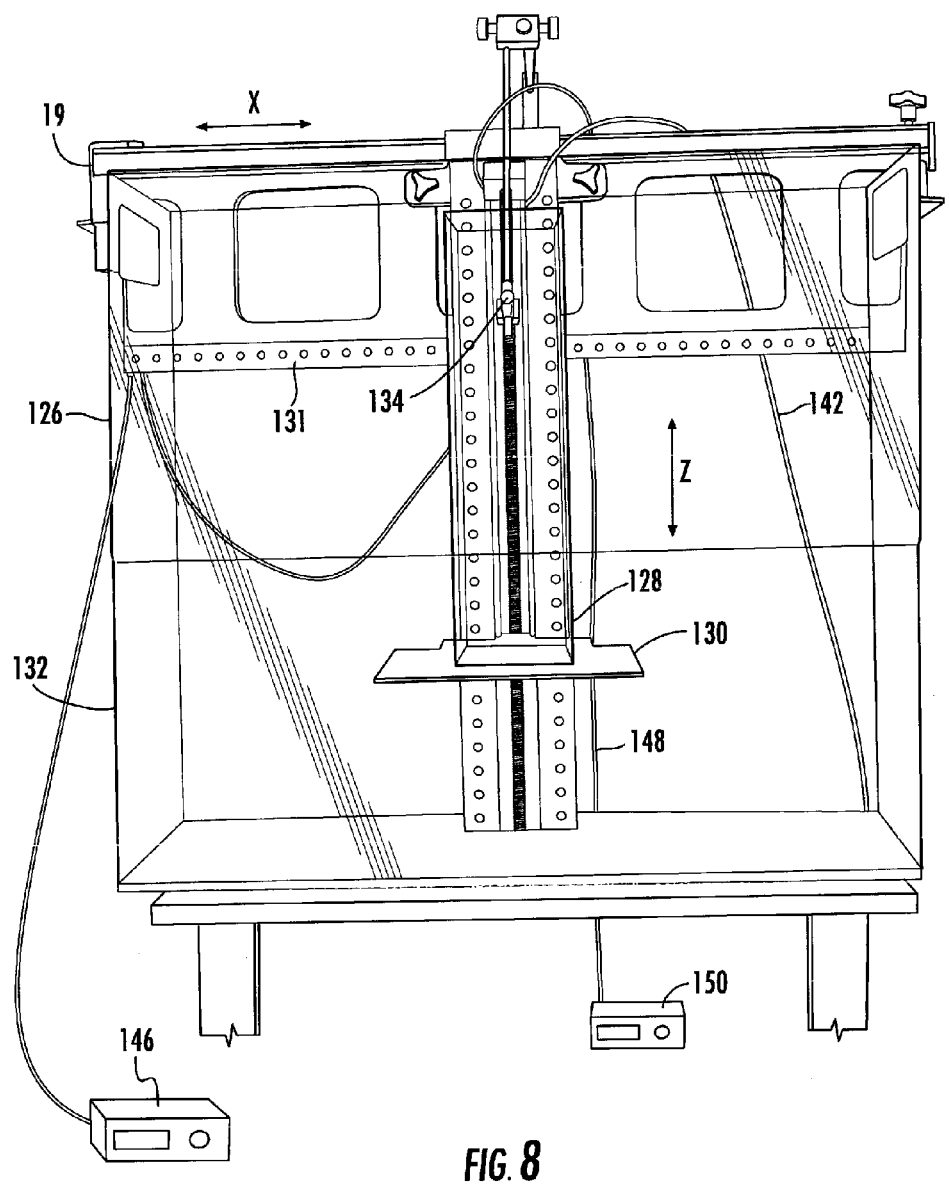
FIG. 8 is a front view of one embodiment of the present invention incorporating the small tank with the detector in a raised position.
Figure 9:
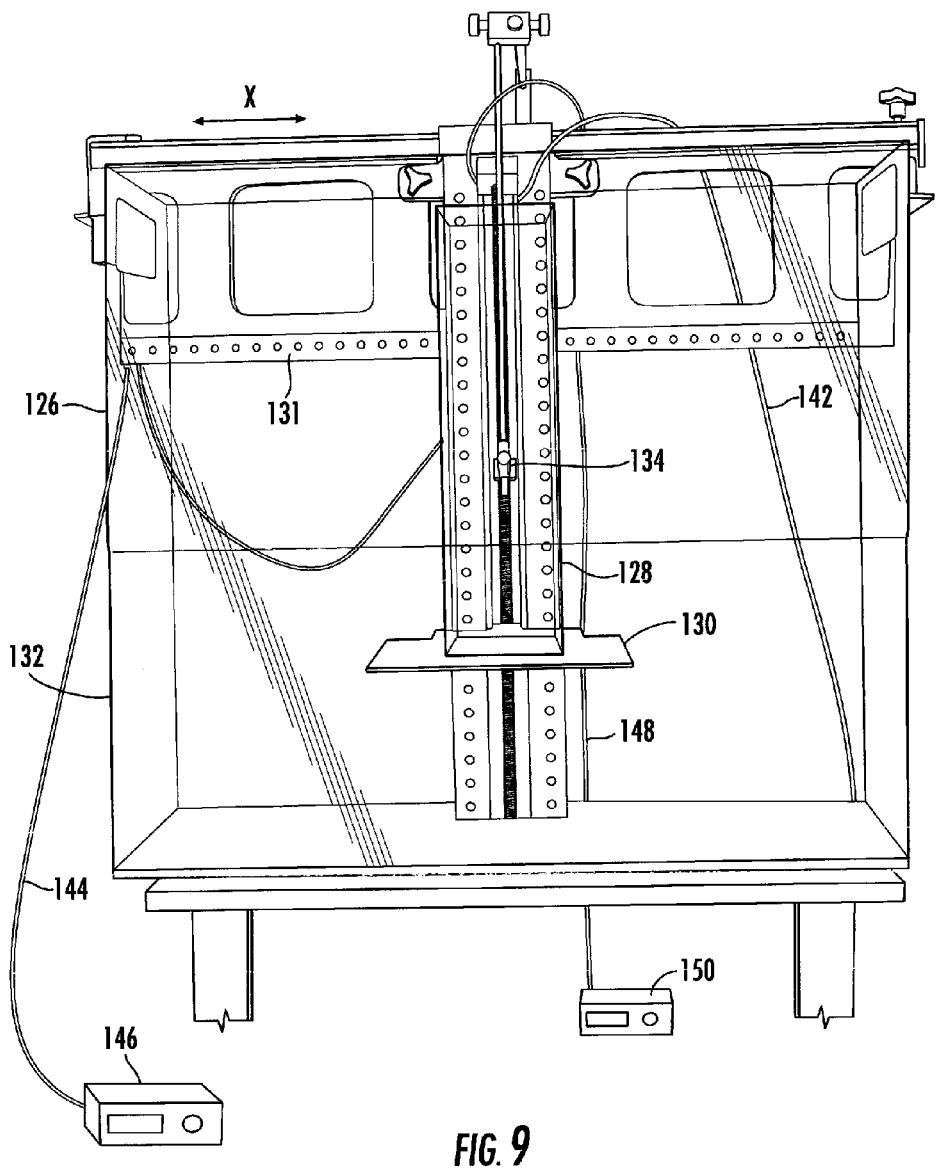
FIG. 9 is a front view of one embodiment of the present invention incorporating the small tank with the sensor in a lowered position.
Figure 10:
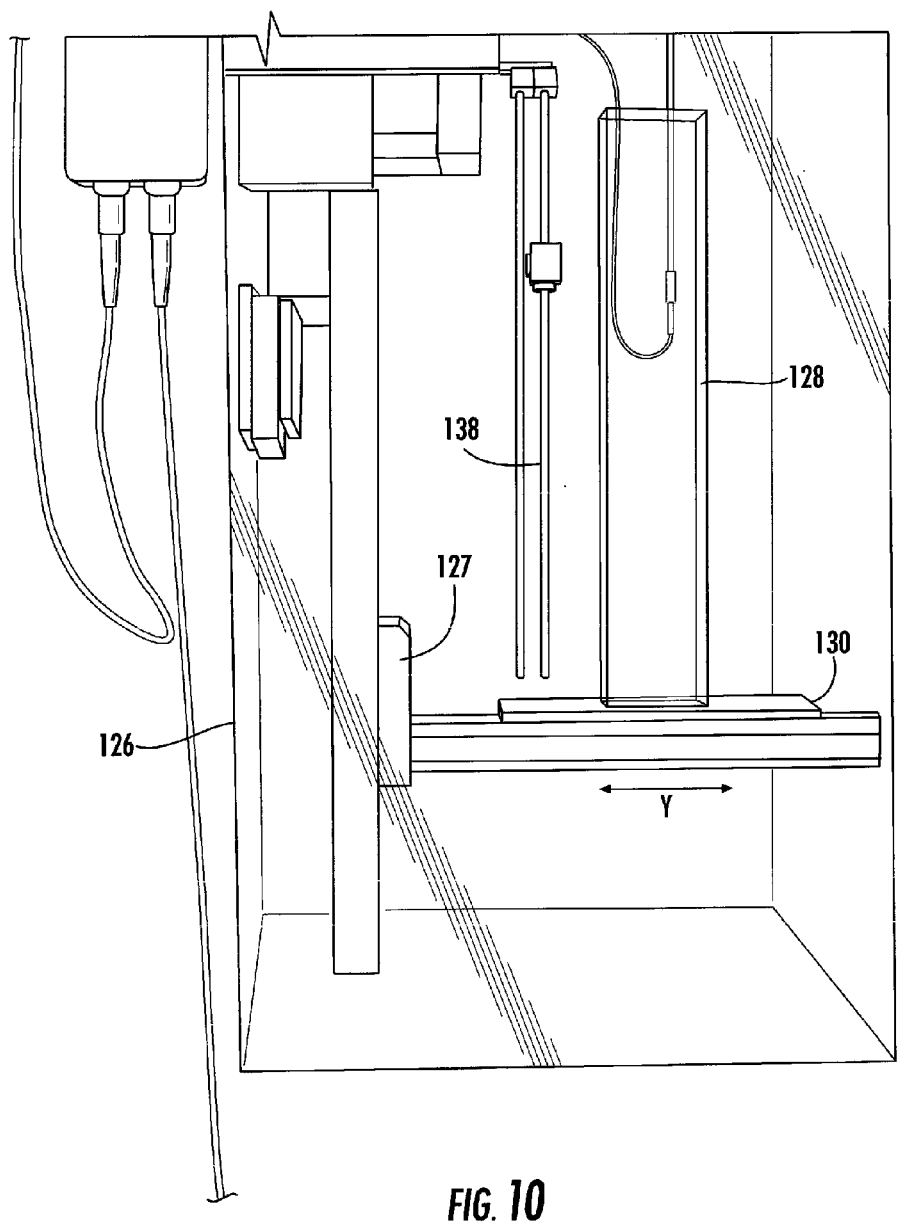
FIG. 10 is a side view of one embodiment of the present invention incorporating the small tank with the detector in a raised position.

The relatively small tank 128 of this second embodiment of the present invention is placed onto a carriage 130 of a measurement device. A portable folding frame 131 (FIGS. 8 and 9) holds the whole system. The modular radiation beam analyzer 126 enables the carriage 130 to be moved in three different axes, X, Y and Z. The X axis extends in a horizontal direction along a portion of the tank 132 and is illustrated in FIGS. 8 and 15. The Z axis extends in a vertical direction and can also be seen in FIGS. 8 and 15. The Y axis extends toward and away from a rear wall of tank 132 and can be seen in FIGS. 3 and 10. Small motors, such as a stepper, servo or digital motor, move the carriage 130 along all three axes. While a stepper motor is a preferred embodiment, any type of motor or device which can move the carriage 130 alone each of the three axes can be utilized.

Figure 11:
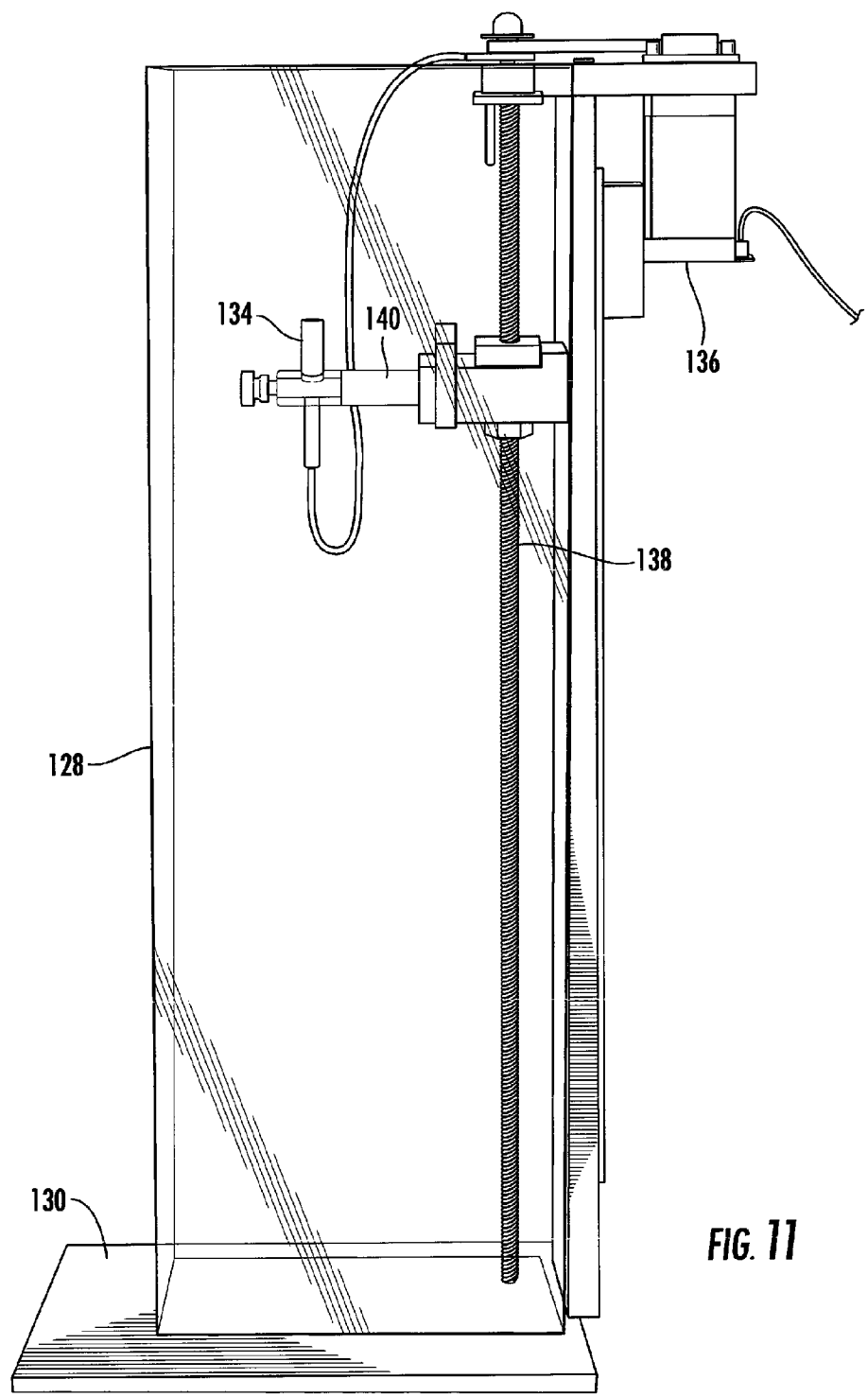
FIG. 11 is a side view of the small tank of one embodiment of the present invention with the detector in a raised position.
Figure 12:
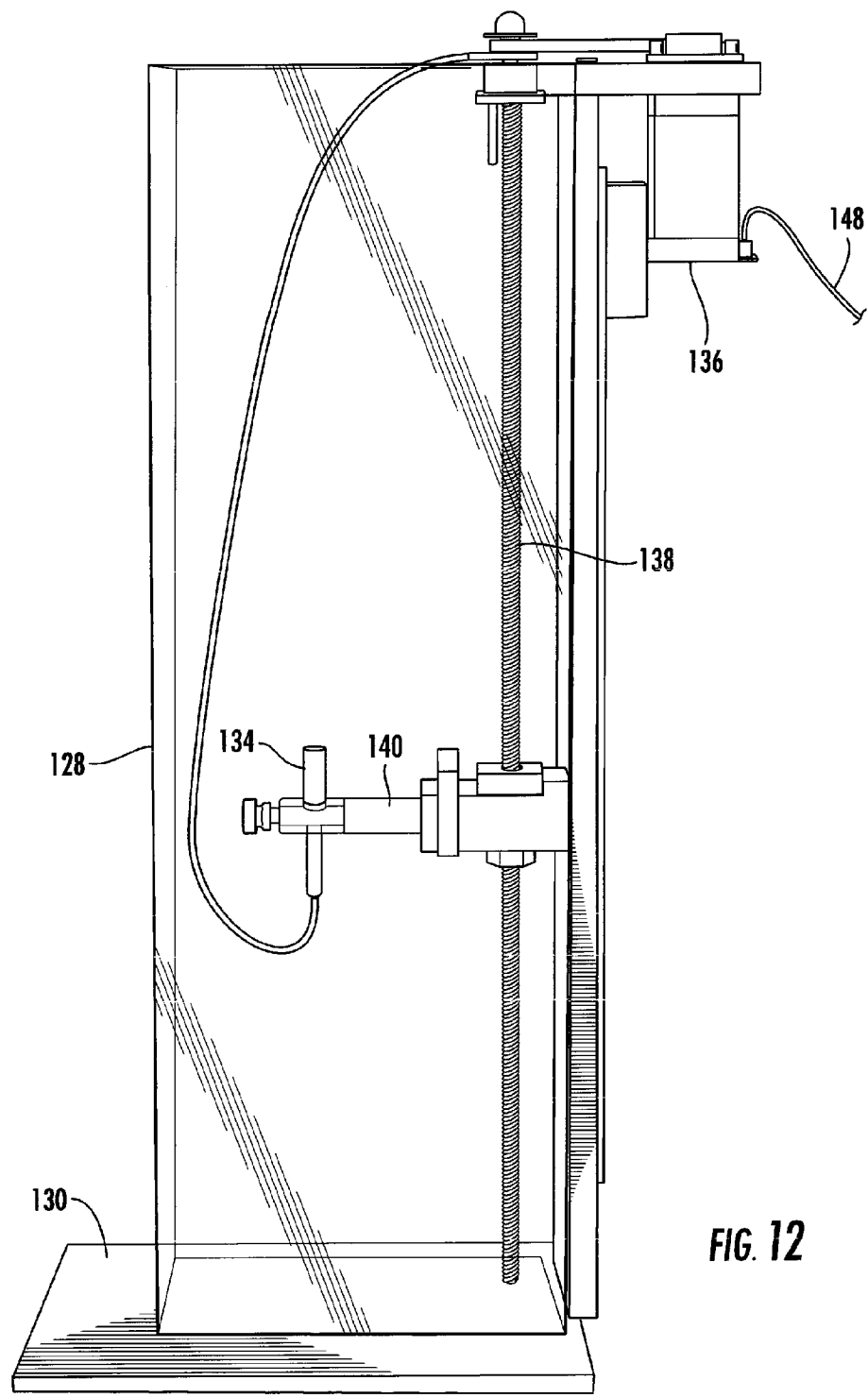
FIG. 12 is a side view of the small tank of one embodiment of the present invention with the detector in a lowered position.
Figure 13:
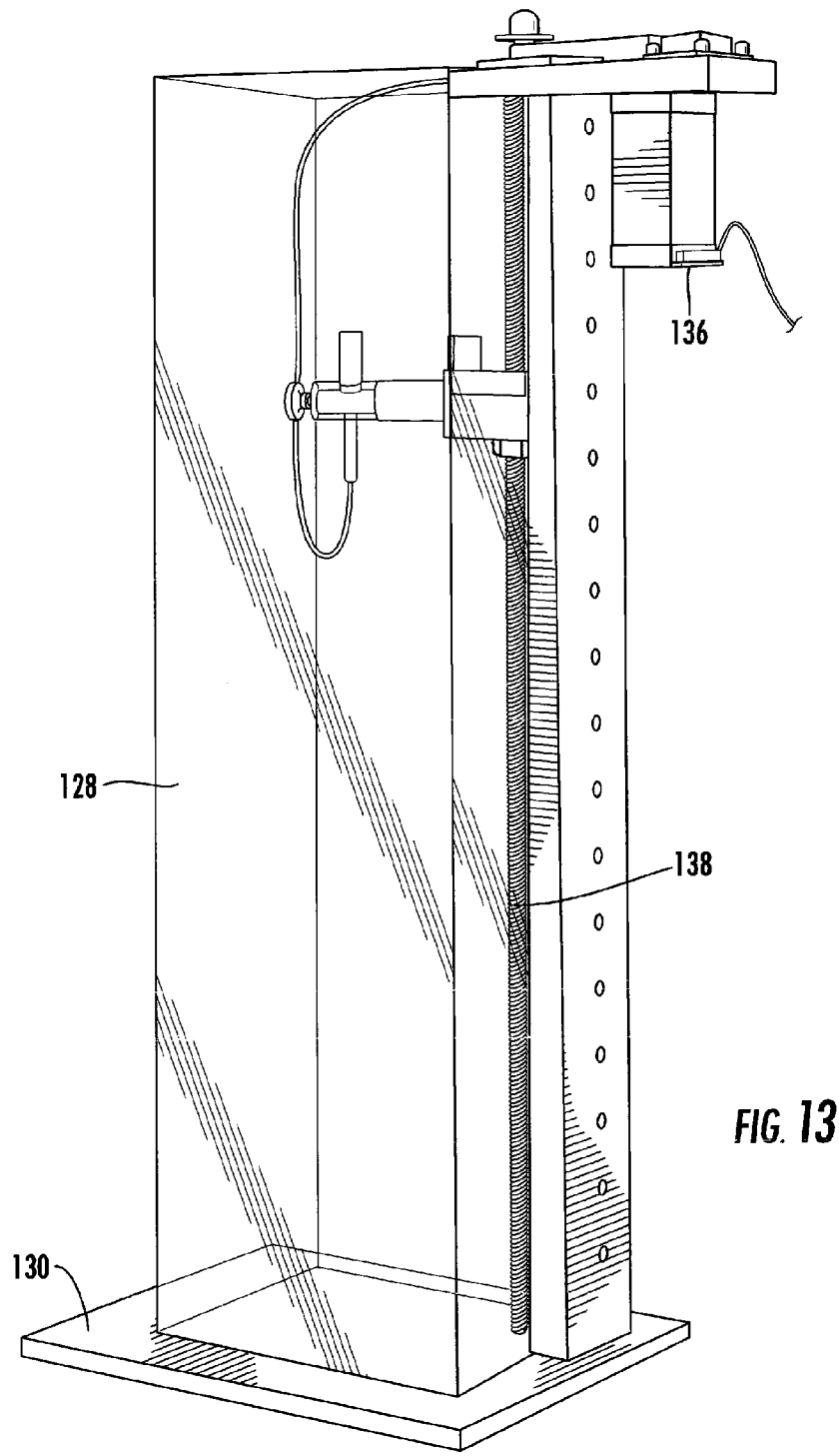
FIG. 13 is a rear perspective view of the small tank of one embodiment of the present invention with the detector in a raised position.
Figure 14:
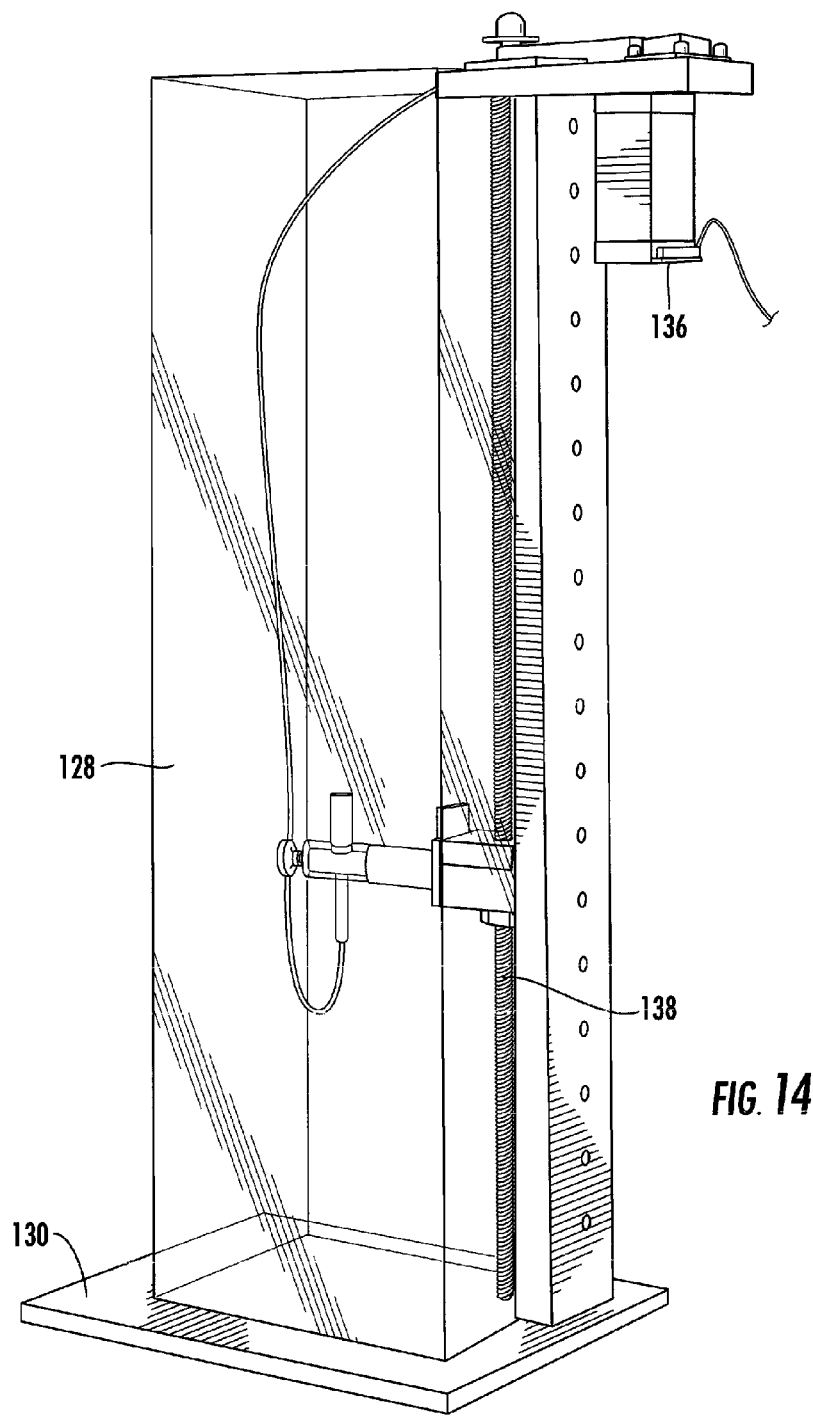
FIG. 14 is a rear perspective view of the small tank of one embodiment of the present invention with the detector in a lowered position.

This second embodiment of the present invention includes a small tank 128 which is movable in the Z direction by motor 127 (FIG. 10) and a detector or sensor 134 which is movable in the Z direction also. A small motor, such as a stepper motor 136, rotates a screw 138 in both a clockwise and counter clockwise direction, as illustrated in FIGS. 11 and 12. A mounting support 140 holds and retains the detector or sensor 134 in a fixed position. The mounting support 140 is secured to and supported on the screw 138 such that when the screw rotates in one direction the mounting support 140 will be raised, relative to the bottom of the tank 132, and when the screw is rotated in the opposite direction the screw will be lowered. While a preferred mounting support 140 is illustrated which applies a transverse force on detector or sensor 134, any other type of mounting support 140 could also be employed. The mounting support 140 permits the distance between the isocentric radiation beam source 112 and the detector or sensor 134 to be adjusted to simulate the distance between a commercial isocentric radiation beam and the malady of an individual or patient to be treated utilizing the radiosurgery system described above. The mounting support 140 also permits the detector or sensor 134 to be aligned with the radiation beam 124 from the isocentric radiation beam source 112.

In radiosurgery systems which utilize the isocentric radiation beam, the distance between the isocentric radiation beam source 112 and the malady being treated on a patient, such as a tumor, remains constant. Thus, in order to simulate the different positions or depths in a patient's body that the tumor or other malady being treated may be located, only the relative depth of the water, which simulates the depth of the item within a patient's body, needs to be varied. Once the correct depth or position within a patient's body is simulated by moving detector or sensor 134 to a specific depth in the water within the tank 128, the amount of radiation from the radiation beam source can be regulated to properly treat the tumor or malady. This second embodiment of the present invention accomplishes this by utilizing one of three methods. The first method maintains the position of sensor 134 fixed, utilizing a mounting support 140 designed to retain the detector, and raises or lowers the small tank of water 128. The second method moves the detector or sensor 134 up or down with a raising and lowering mechanism in one direction and synchronically moves the small tank of water in the opposite direction with another raising and lowering mechanism. The second method also keeps the SAD constant. These methods position the detector relative to the radiation source to simulate the location of a malady within a patient's body. This movement of the tank permits the radiation from the isocentric radiation beam source to be properly isocentrically measured. Main difference between the three methods: the second method uses an extra motor, extending the scanning capability to three (3) axes X, Y, Z, therefore scanning in depth, and radial transverse and diagonal directions. The third method utilizes the treatment table to provide controlled rotation to the testing device to extend the scanning capability to three axes. The first method can scan only in depth and transverse directions. When two of the motors are simultaneously operated, the object being moved by these motors, the carriage 130 and/or the second tank 128, is/are moved is a direction between or diagonal to the two axes of movement of the object. For example, the X and Y axes, the X and Z axes, the Y and Z axes. As an example, if the motor 19 moves an object along the X axis and motor 21 moves the object along the Y axis, then when motors 19 and 21 are operated simultaneously the object moves on a diagonal between the X and Y axes. Also, motor 45 moves an object along the Z axis, so that when motor 45 and motor 21 are operated simultaneously the object moves between the Z and Y axes. Finally, motor 45 moves an object along the Z axis, so that when motor 45 and motor 19 are operated simultaneously the object moves between the Z and X axes.

The first method raises and/or lowers the tank of water 128 by raising and/or lowering the carriage 130 with stepper motors or similar devices capable of raising and/or lowering the carriage. The second method raises and/or lowers the detector or sensor 134 by raising and/or lowering the mounting support 140 utilizing a screw mechanism 138 and stepper motor 136 or similar device which can raise and/or lower the support. Simultaneously the tank 128 is raised and/or lowered by raising and/or lowering the carriage 130 as described herein above. The motor(s) or device(s) which raise and/or lower the mounting support 140 and the motor(s) or device(s) which raise and/or lower the carriage 130 are synchronized to maintain the detector or sensor 134 in a fixed position relative to the radiation source. In other words to keep the SAD constant.

As illustrated, tank 128 is 8 cm long, 8 cm wide and 40 cm high. It has a capacity of 2.5 liters. It is made from a clear acrylic material. In a preferred embodiment, the tank 128 is cylindrical having a diameter of 19 cm and a height of 40 cm. Tanks having various other dimensions and weights can also be utilized. Tanks can also be made from various other materials.

A wire or cable 142 extends from the detector or sensor to a recording device to measure and record the amount of radiation delivered to a specific point by the radiation source. Another wire or cable 144 extends from a control box 146, FIG. 9. The control box controls the movement of the carriage 130 in the X, Y and Z directions. Another wire or cable 148 extends from the motor 136 to a control device 150. This control device 150 synchronizes the movement between the carriage 130 and the mounting support 140 to maintain the detector or sensor in a position fixed relative to the radiation source.

This embodiment of the present invention utilizes the software and programming of applicant's U.S. patent application Ser. No. 61/083,740, filed Jul. 25, 2008, entitled, "Modular Radiation Beam Analyzer Software" and U.S. patent application Ser. No. 11/510,275, filed Aug. 25, 2006, entitled, "Convertible Radiation Beam Analyzer System" to control the motors which operate the guideways, to acquire data, to analyze the data, to provide graphical representations of the data and to transfer data with the pertinent modifications.

This embodiment of the present invention can be used with a single or an array of ion chambers. It can also be used with a single or an array of diodes. This embodiment of the present invention can also be utilized with Cyberknife® or conventional radiation therapy. When used with conventional radiation therapy, the dimensions of the tank 128 are 14 cm long by 14 cm wide by 40 cm high. But the main applications are measurements of small fields, like the ones used in Cyberknife® machines and stereotactic procedures.

Figures 16A, 16B:
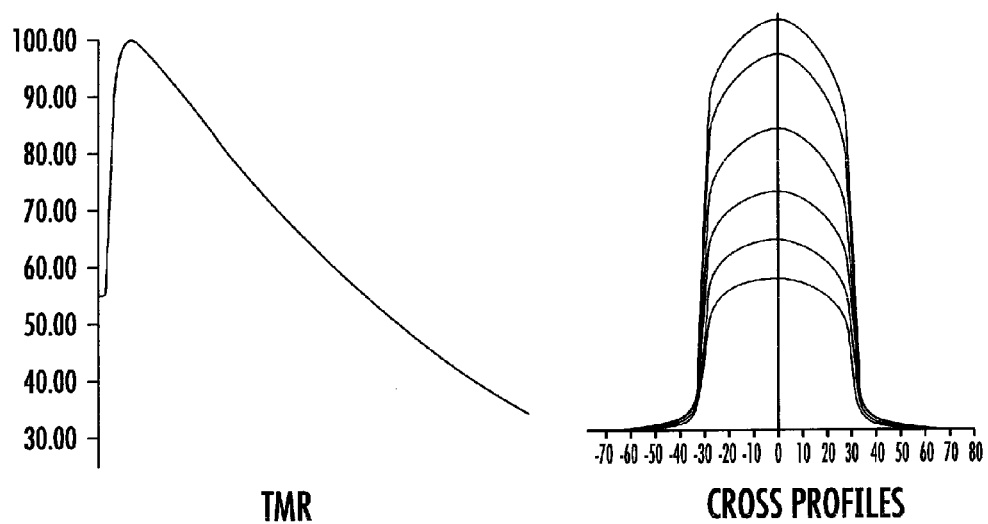
FIGS. 16A and 16B are the results of an isocentric depth scan (TPR) and a cross profile.

When scanning in the Z direction, the isocentric scanning generates the TMR/TPR function. This is accomplished using either one of the two methods described herein before. This is different from a conventional scanner which does not keep the SAD constant and generates a PDD (percentage depth dose) function. It should also be noted that TMR (Tissue Maximum Ratio) cannot scan across profiles isocentrically. It is further noted that dynamic phantom measurements cannot scan depths isocentrically. Results of an isocentric depth scan (TMR) and cross profiles are illustrated in FIGS. 16A and 16B.

Figure 17:
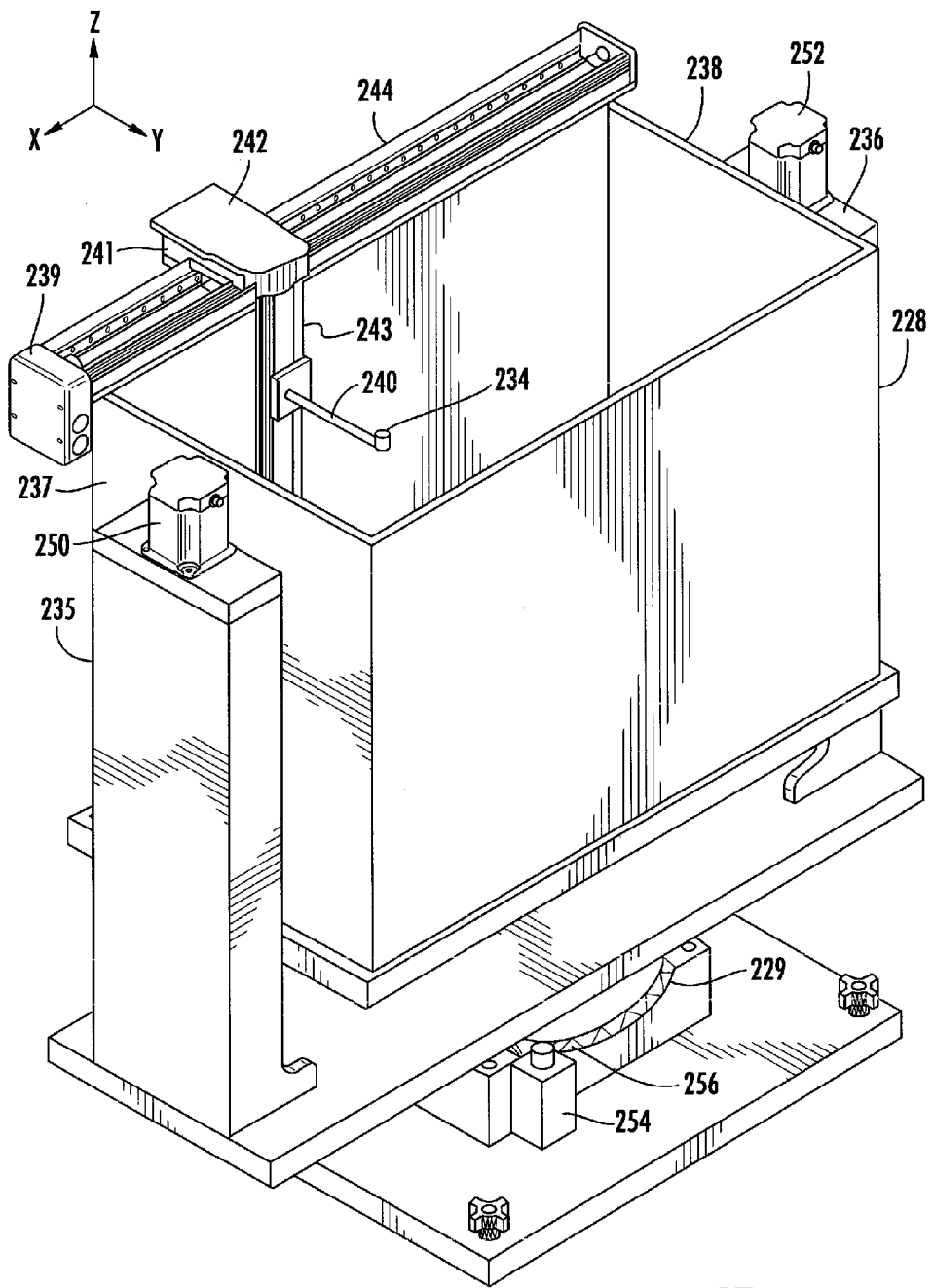
FIG. 17 is a perspective view of one embodiment of the present invention.

Referring to FIG. 17, a third embodiment of the present invention will now be described. This third embodiment operates and is used in the same manner as the first two embodiments of the invention to perform direct measurements of TMP/TPR_SAD (equivalent to isocentric measurements) with the radiation being imparted from a source (not shown) on the top of the tank 228. The radiation source could be the same as 12 and 112, illustrated in FIGS. 1 and 7 respectively. A tank 228 which contains a phantom body of water is mounted onto a rotary table 229 (FIG. 17). The rotary table 229, which supports tank 228, is placed on a movable table similar to the movable table 118 (FIG. 7), to measure the distribution and intensity of the radiation beam in the radiosurgery system, as illustrated in FIG. 7. In the radiation treatment planning currently employed in the prior art, the input sent to the radiation treatment planning computerized system is from non-isocentric data (SSD) (source to surface distance) which is then converted to isocentric data (SAD). This presents two major problems. First, the conversion algorithms used for the conversion are complicated. Second, the results are inaccurate. Additionally, the present invention provides a system having a modular design which can be applied to a 1-D (imensional), 2-D and 3-D systems.

Tank 228 can be rotated about the Z axis by a rotary table 229. A first plurality of rails 235, 236 are secured to the left 237 and right 238 sides of the tank 228 (FIG. 17). Linear slide rails (not shown) are mounted in the rails 235 and 236. These linear slide rails are preferably the linear slide rails manufactured by IKO Nippon Thompson Company, LTD. However, other equivalent linear slide rails could also be employed. Two motors 250 and 252 or similar devices move tank 228 along rails 235, 236 in upward and downward directions. This motion moves the tank 228 in the Z direction. This construction enables the entire device to be rotated about the Z axis by a motor or similar device (not shown). This rotary table 229 positions the system at any desired angle to allow diagonal and/or transverse scanning by detector 234.

A device 242 moves the vertical arm 243 along guideway 244 by a motor or similar device 239. This can be accomplished automatically or manually. This motion along guideway 244 also moves the detector 234 along the X axis. The detector or sensor 234 is mounted on a support 240. The support 240 can be moved vertically up and down along the Z axis by motor 241 (FIGS. 17 and 18) or similar device either automatically or manually. Motor 241 moves detector 234 vertically. The two motors 250 and 252 move the tank 228 vertically along the Z axis. Motors 241, 250, and 252 can be operated simultaneously and in opposite directions so that the detector 234 will remain stationary. This is accomplished by operating motor 241 in one direction and both motors 250 and 252 in the opposite direction. This operation permits isocentric scanning of the radiation beam.

By moving the detector 234 along the X and Z axes, scanning is accomplished transversely and in depth with respect to the radiation beam and treatment site in an individual, the object being measured. The rotary table 229 permits scanning in the radial and diagonal directions with respect to the radiation beam and treatment site in an individual, the object being measured. Thus, motions along the X, Y, and Z axes provide a device and system which can scan in depth, in a radial direction, in a transverse direction, and in a diagonal direction with respect to the object being measured.

This operation permits isocentric scanning of the radiation beams. In this method the source to the axis (target, probe, radiation detector) distance SAD remains constant. This is a preferred method of treatment of the patient. This method also permits a direct measurement of isocentric beams which range from 0.4 cm to 40 cm field sizes. Other methods of measurement of isocentric radiation beams only allow field sizes of 0.4 cm to 6 cm. Non isocentric measurements, on the other hand, can cause significant errors (up to 20%), especially in the small fields of stereotactic treatment.

The third embodiment enables measurements of substantially larger fields than the first two embodiments without the use of a large tank of water. This is accomplished by rotating tank 228 up to 90 degrees from a first position to a second position. This movement enables detector 234 to be moved over a substantially larger area without employing a large tank. The use of the thinner tank 228, in the Y direction, on a rotary base, results in a significant reduction in the size of the tank and volume of water required to make measurements in large fields. This also results in a significant weight savings because of the relative small volume of water used: 16 gallons vs. 50 gallons in a conventional tank. A preferred tank is 35 cm long, 30 cm wide, 40 cm high, and made from an acrylic material.

Figure 18:
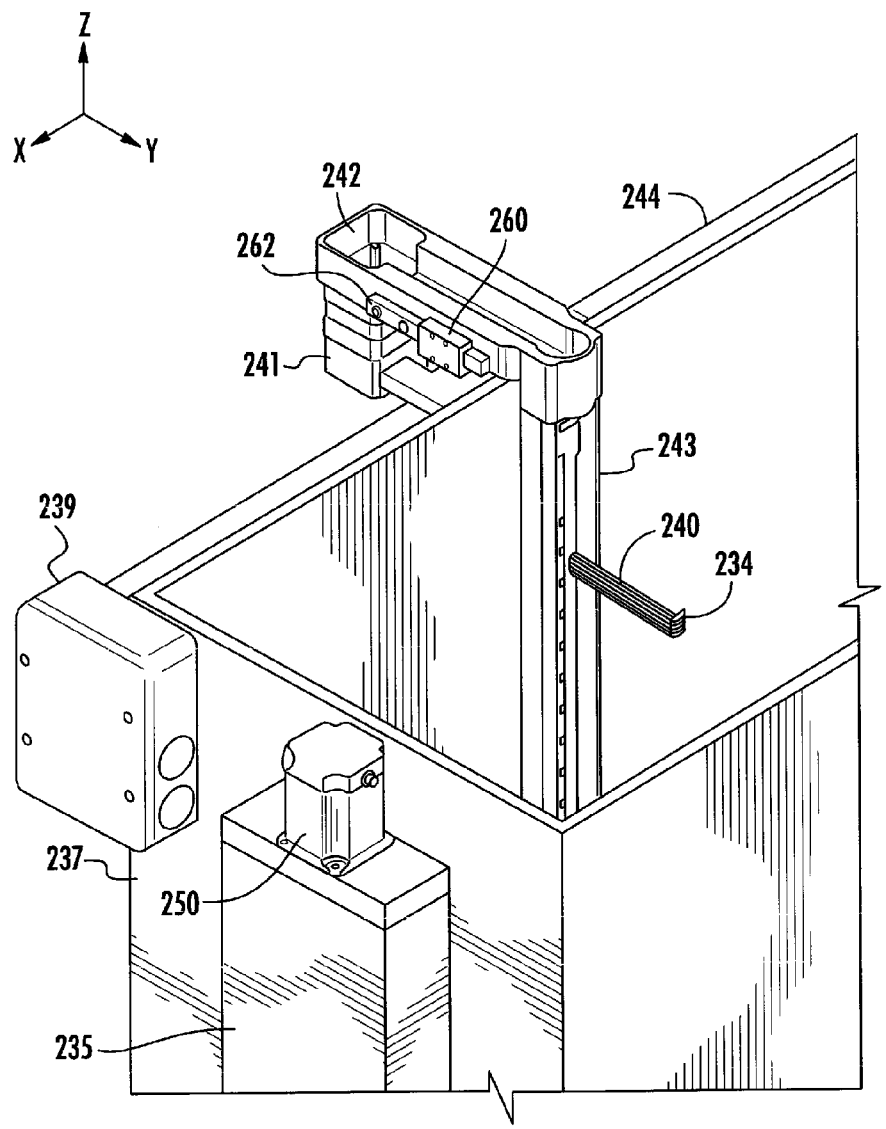
FIG. 18 is a perspective view of one embodiment of the present invention.

A fourth embodiment of the present invention is illustrated in FIG. 18. In this embodiment a small stepper motor or similar device 260 is secured to one side of the device 242. A track 262 or rod with teeth that interact with a gear is secured to the device 242 on the same side as the motor 260. A controller operates the motor 260 which moves the device 242 and attached detector 234 in the Y direction, toward and away from the rear wall of tank 228. The motor 260 can be operated in conjunction with motor 239 to permit the detector 234 to move in a diagonal direction between the Y and X axes. Motor 260 can also be operated in conjunction with motors 250 and 252 to permit the detector 234 to move in a diagonal direction between the Z and Y axes.

In a fifth embodiment of the present invention, a treatment table 118 having a controlled rotation feature which allows the treatment table to be rotated around an axis may be utilized in place of motor 254 and its associated gear train 256 to rotate the tank of water 228. It should be noted that a single stepper or digital motor having suitable torque may be utilized in place of the combination of the motor and gear train to rotate the tank without departing from the scope of the invention. In this method the movement of the X and Y axes are coordinated with the rotation of the treatment table to provide the three axes of controlled movement of the dosemetry probe or sensor 234. The three axes can thereby be controlled to maintain the sensor at a predetermined distance from the accelerator for isocentric testing.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A radiation beam analyzer for detecting radiation dosimetry of a beam emitted along an axis from a radiotherapy treatment device comprising:
    a phantom body formed of a material having a density proximate that of a human body;
    a tank containing said phantom body;

at least one dosimetry probe constructed and arranged to sense photons and electrons, said at least one dosimetry probe positioned within said phantom body;

a plurality of rails secured to said tank and said phantom body;

a rotary table, said tank and said plurality of rails being positioned on said rotary table; and a plurality of mechanisms incrementally moving said tank and said phantom body in a substantially vertical, radial, transverse or diagonal direction relative to a radiation source;

the distance between said radiation source and the axis of a beam emitted from said radiation source relative to said at least one dosimetry probe being constant;

whereby movement of said tank and said phantom body through a series of locations is carried out so as to provide sufficient data to determine the proper dose of radiation required for radiotherapeutics.

2. The radiation beam analyzer of claim 1 wherein said dosimetry probe is an ion chamber.

3. The radiation beam analyzer of claim 1 wherein said radiation beam analyzer directly measures radiation from isocentric beams in a field of approximately 0.4 cm to 40 cm.

4. The radiation beam analyzer of claim 1 wherein said movement is isocentric.

5. The radiation beam analyzer of claim 1 wherein said radiotherapy treatment device is a linear accelerator.

6. The radiation beam analyzer of claim 1 wherein said dosimetry probe is at least one diode.

7. The radiation beam analyzer of claim 1 wherein said rotary table includes a motor and a gear train, said motor and said gear train constructed and arranged to provide rotation about an axis upon operation of said motor.

8. The radiation beam analyzer of claim 7 wherein said rotary table is a treatment table.

9. A radiation beam analyzer for detecting radiation dosimetry of a beam emitted along an axis from a radiotherapy treatment device comprising:

a phantom body formed of a material having a density proximate that of a human body;

a tank containing said phantom body;

at least one dosimetry probe constructed and arranged to sense photons and electrons, said at least one dosimetry probe positioned within said phantom body;

a plurality of rails secured to said tank and said phantom body;

a rotary table, said tank, and said plurality of rails being positioned on said rotary table;

a plurality of mechanisms incrementally moving said tank and said phantom body in a substantially vertical, radial, transverse or diagonal direction relative to a radiation source; and a controller connected to and operating said plurality of mechanisms to move both said tank and said at least one dosimetry probe to maintain a distance between said radiation source and an axis of a beam emitted from said radiation source relative to said at least one dosimetry probe constant;

whereby movement of said phantom body and said at least one dosimetry probe through a series of locations is carried out so as to provide sufficient data to determine the proper dose of radiation required for radiotherapy treatment.

10. The radiation beam analyzer of claim 9 wherein said dosimetry probe is an ion chamber.

11. The radiation beam analyzer of claim 9 wherein said radiation beam analyzer directly measures radiation from isocentric beams in a field of approximately 0.4 cm to 40 cm.

12. The radiation beam analyzer of claim 9 wherein said movement is isocentric.

13. The radiation beam analyzer of claim 9 wherein said radiotherapy treatment device is a linear accelerator.

14. The radiation beam analyzer of claim 9 wherein said dosimetry probe is at least one diode.

15. The radiation beam analyzer of claim 9 wherein said rotary table includes a motor and a gear train, said motor and said gear train constructed and arranged to provide rotation about an axis upon operation of said motor.

16. The radiation beam analyzer of claim 15 wherein said rotary table is a treatment table.

17. A method of calibrating a radiotherapy treatment device comprising:

providing a source of radiation along an axis;

providing a phantom body formed of a material having a density proximate that of a human body;

providing a tank containing said phantom body;

providing at least one dosimetry probe constructed and arranged to sense photons and electrons;

positioning said at least one dosimetry probe within said phantom body;

providing a plurality of rails secured to said tank and said phantom body;

providing a rotary table;

positioning said tank and said plurality of rails on said rotary table;

incrementally moving said tank and said phantom body in a substantially vertical, radial, transverse or diagonal direction relative to said radiation source; and employing a controller to simultaneously move both said tank and said at least one dosimetry probe relative to each other while maintaining the distance between said radiation source and the axis of a beam emitted from said radiation source relative to said at least one dosimetry probe substantially constant;

whereby movement of said phantom body through a series of locations is carried out so as to provide sufficient data to determine the proper dose of radiation required for radiotherapy treatment.

18. The method of calibrating a radiotherapy treatment device of claim 17 wherein one of said plurality of rails is a Z-axis guideway constructed and arranged to traverse said dosimetry probe.

19. The method of calibrating a radiotherapy treatment device of claim 17 wherein one of said plurality of rails is a Y-axis guideway constructed and arranged to traverse said tank.

20. The method of calibrating a radiotherapy treatment device of claim 17 wherein one of said plurality of rails is a X-axis guideway constructed and arranged to traverse said dosimetry probe.

* * * * *